United States Patent
Schlereth et al.

(10) Patent No.: US 10,295,504 B2
(45) Date of Patent: May 21, 2019

(54) PIEZOELECTRIC SENSORS AND QUARTZ CRYSTAL MONITORS

(71) Applicants: Fritz H. Schlereth, Syracuse, NY (US); James Spencer, Fayetteville, NY (US)

(72) Inventors: Fritz H. Schlereth, Syracuse, NY (US); James Spencer, Fayetteville, NY (US)

(73) Assignee: SYRACUSE UNIVERSITY, Syracuse, NY (US)

( * ) Notice: Subject to any disclaimer, the term of this patent is extended or adjusted under 35 U.S.C. 154(b) by 0 days.

(21) Appl. No.: 15/698,762

(22) Filed: Sep. 8, 2017

(65) Prior Publication Data

US 2018/0074024 A1    Mar. 15, 2018

Related U.S. Application Data

(60) Provisional application No. 62/393,426, filed on Sep. 12, 2016.

(51) Int. Cl.
| | |
|---|---|
| *G01N 29/24* | (2006.01) |
| *H01L 41/08* | (2006.01) |
| *H01L 41/18* | (2006.01) |
| *H01L 41/113* | (2006.01) |
| *H01L 41/193* | (2006.01) |
| *G01N 29/12* | (2006.01) |

(52) U.S. Cl.
CPC ......... *G01N 29/2443* (2013.01); *G01N 29/12* (2013.01); *H01L 41/0825* (2013.01); *H01L 41/1132* (2013.01); *H01L 41/18* (2013.01); *H01L 41/183* (2013.01); *H01L 41/193* (2013.01); *G01N 2291/012* (2013.01); *G01N 2291/014* (2013.01); *G01N 2291/024* (2013.01); *G01N 2291/0215* (2013.01); *G01N 2291/0426* (2013.01)

(58) Field of Classification Search
CPC .......................... G01N 29/2443; G01N 29/12; H01L 41/0825; H01L 41/1132; H01L 41/18; H01L 41/183; H01L 41/193
USPC ....................................................... 422/82.11
See application file for complete search history.

(56) References Cited

U.S. PATENT DOCUMENTS

| | | | |
|---|---|---|---|
| 7,362,415 B2* | 4/2008 | Franken | G03F 7/70291 355/30 |
| 2006/0210440 A1* | 9/2006 | Potyrailo | G01N 21/1702 422/82.01 |
| 2010/0066346 A1* | 3/2010 | Zhang | B81C 1/00166 324/71.1 |

* cited by examiner

*Primary Examiner* — Jill A Warden
*Assistant Examiner* — Jacqueline Brazin
(74) *Attorney, Agent, or Firm* — Bond Schoeneck and King PLLC; David Nocilly; George McGuire

(57) ABSTRACT

Surface modifications and improvements to piezoelectric-based sensors, such as QCMs and other piezoelectric devices, that significantly increase the sensitivity and the specificity (selectivity). These modifications can comprise mechanical and chemical changes to the surfaces of the sensors, either individually or together. For example, nano-size structures may be provided on the surface to improve sensitivity. Additionally, chemical coatings may be tethered to the surfaces, walls, or crystal to provide targeted sensitivity. Additionally, porous, layered and multiple sensor arrays may be formed to enhance sensitivity and selectivity.

5 Claims, 15 Drawing Sheets

PIEZOELECTRIC SENSORS AND QUARTZ CRYSTAL MONITORS

CROSS-REFERENCE TO RELATED APPLICATIONS

The present application claims priority to U.S. Provisional Application No. 62/393,426, filed on Sep. 12, 2016.

BACKGROUND OF THE INVENTION

1. Field of the Invention

The present invention relates to piezoelectric sensors and, more specifically, to improvements to the surface of a quartz crystal monitor and related piezoelectric substrates.

2. Description of the Related Art

The QCM (Quartz Crystal Monitor) is an instrument in wide use for mass measurement. Early applications of these devices were focused on the measurement of thickness of a deposit in semiconductor manufacture. Initially the QCM was developed for the semiconductor industry to provide a means for real-time measurement of deposit thickness in the manufacture of semiconductor devices. Since that time, applications of QCM-based devices have broadened, particularly when it was discovered that the quartz crystal would operate in liquids as well as in air, and vacuum. More recently the range of applications has grown to include biochemical and environmental monitoring, explosives detection, intrusion detection. However, the sensitivity and specificity of sensors needs to improve to adequately address these new applications. Accordingly, there is a need in the art to improve the sensitivity and specificity of QCMs and other piezoelectric-based sensors for new applications.

BRIEF SUMMARY OF THE INVENTION

The present invention is an improved sensor having higher sensitivity and, optionally, specificity for target compounds. To improve sensitivity, a sensor enhancement in this invention includes a piezoelectric material having an upper surface with a plurality of upstanding walls positioned on the upper surface, wherein the walls have a height of up to 1000 nanometers, a width of up to 1000 nanometers, and are spaced apart from each other by up to 1000 nanometers. The piezoelectric material may be a piezoelectric composite material or a quartz crystal. A noble metal coating may be positioned on the upper surface of the piezoelectric material. The walls may be coated to reduce elasticity of any collisions between the walls and a particle. To improve selectivity, an additional sensor enhancement in the present invention includes a plurality of tethered linkers that may be attached to the walls or surface of the piezoelectric substrate and additionally attached to a functional group that includes a chemical moiety having specific interaction with a target analyte, including a biochemical molecule having a specific interaction with a target analyte. The third enhancement in this invention is the use of porous, three-dimensional piezoelectric substrates to enhance the surface area of the sensor, thereby increasing both sensitivity and selectivity.

The invention also includes a detector having a chassis, a first chamber mounted to the chassis and enclosing a reference sensor comprising a first quartz crystal having a first upper surface and a first plurality of upstanding walls positioned on the first upper surface, wherein the first plurality of walls have a first height of up to 1000 nanometers, a first width of up to 1000 nanometers, and are spaced apart from each other by up to 1000 nanometers, and a second chamber mounted to the chassis and enclosing a cooling elements, a temperature sensor mounted to the first element, and a detection sensor positioned on the cooling element and comprising a second quartz crystal having a second upper surface and a second plurality of upstanding walls positioned on the second upper surface, wherein the second plurality of walls have a second height of up to 1000 nanometers, a second width of up to 1000 nanometers, and are spaced apart from each other by up to 1000 nanometers. The second chamber includes an inlet for the flow of air into a top of the second chamber and an outlet for the flow of air out of a bottom of the second chamber so that when the detection sensor is cooled by the cooling element and air is drawn into the inlet and out of the outlet, molecules in the air will be deposited on the detection sensor. A second cooling element may be associated with the chamber and configured to maintain the chamber at a difference temperature than the first cooling element maintains the detection sensor. A heat sink is positioned below and proximately to the second chamber. A fan is positioned to blow across the heat sink and the outlet to create a vacuum proximately to the outlet. A temperature sensor is associated with the first cooling element.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 7:
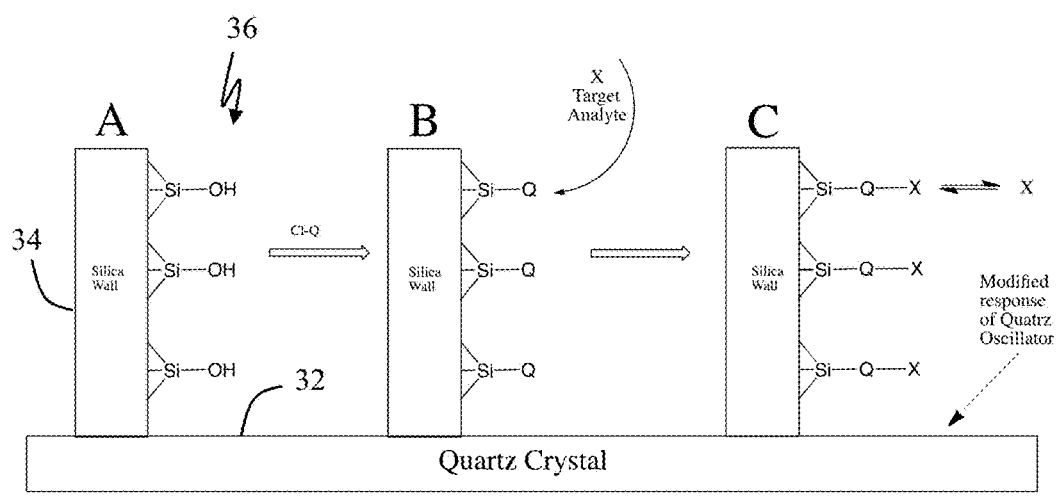
Figure 7:
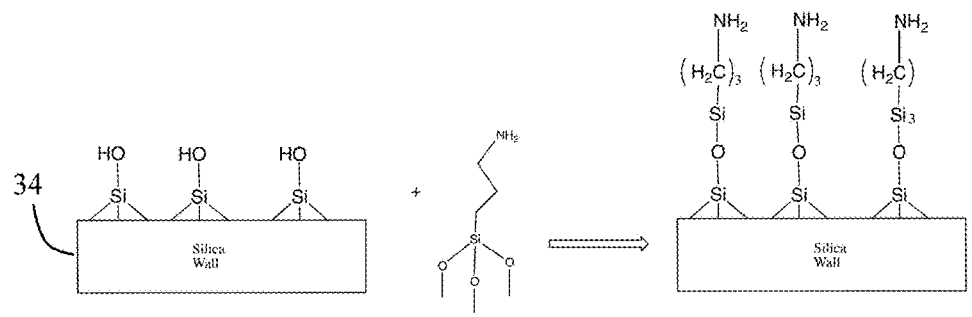
Figure 8:
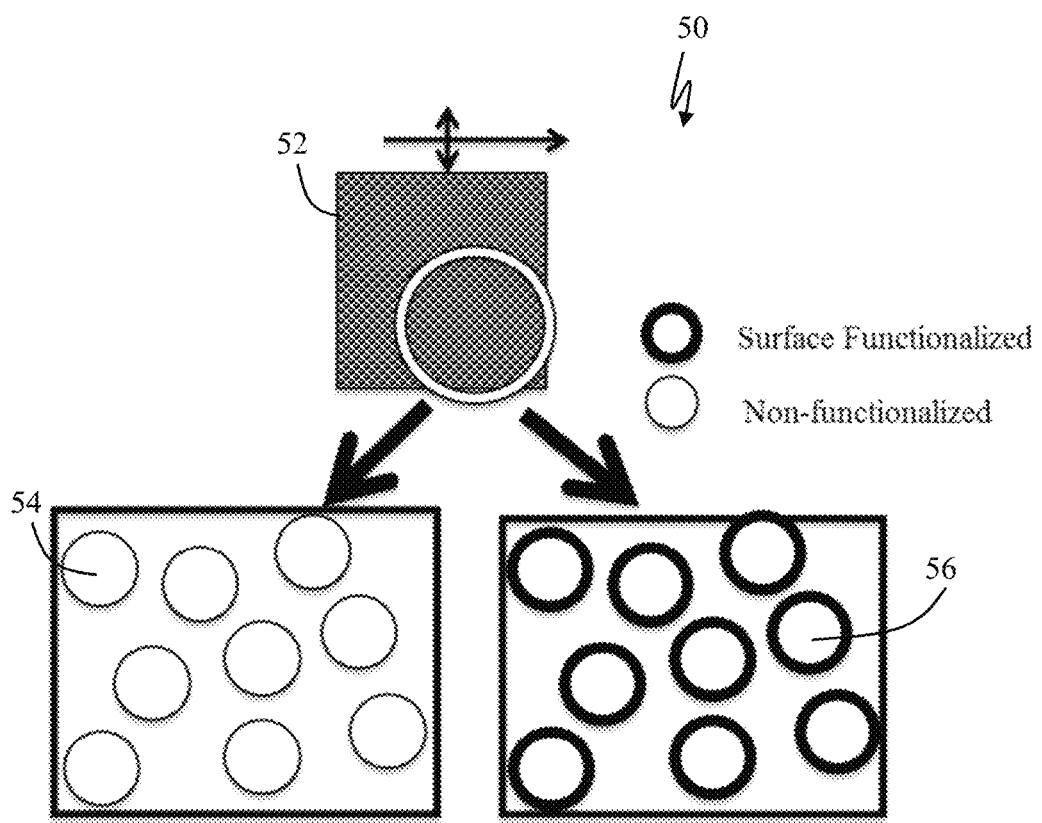
Figure 9:
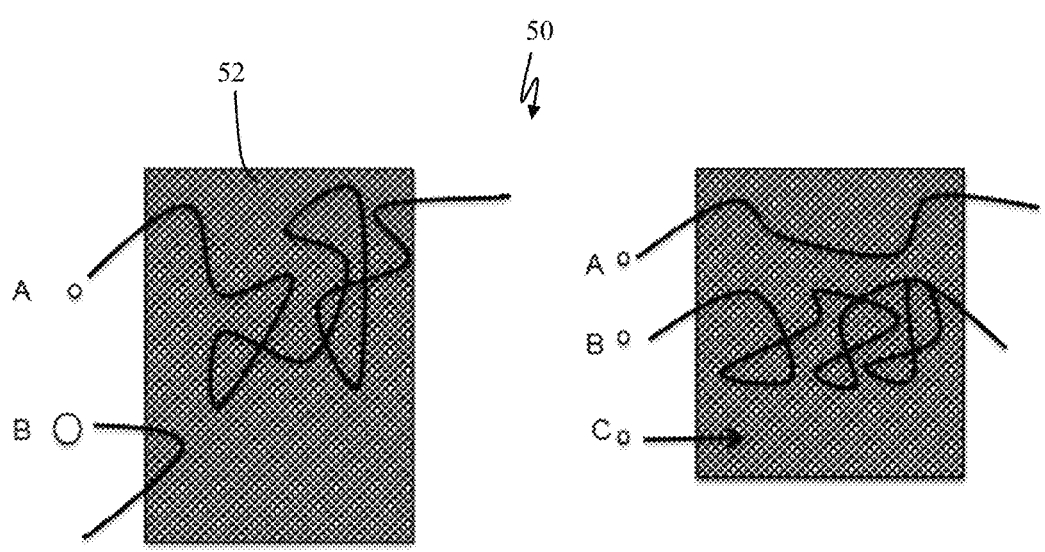
Figure 10:
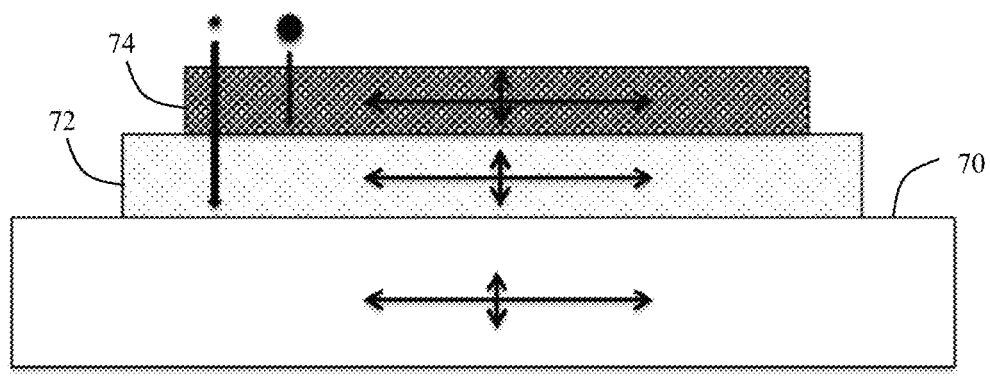
Figure 11:
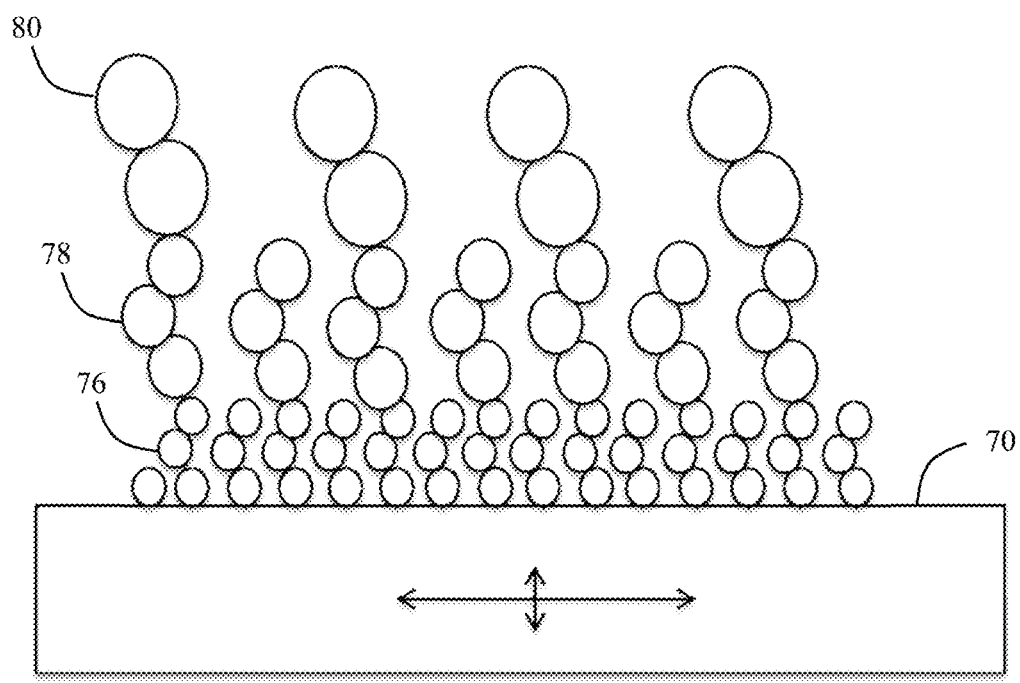
Figure 12:
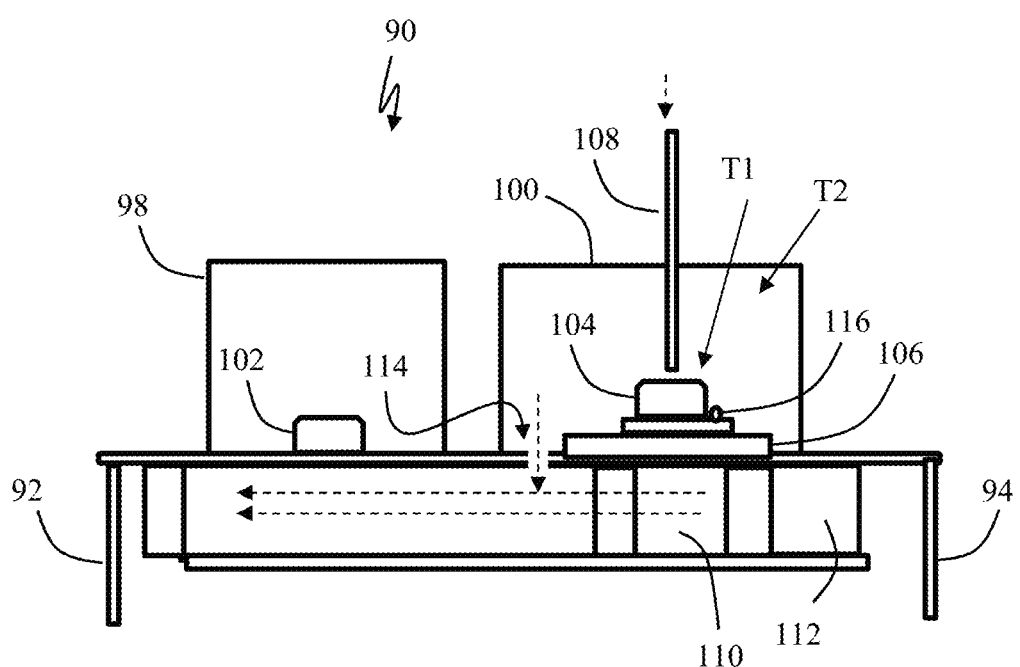
Figure 13:
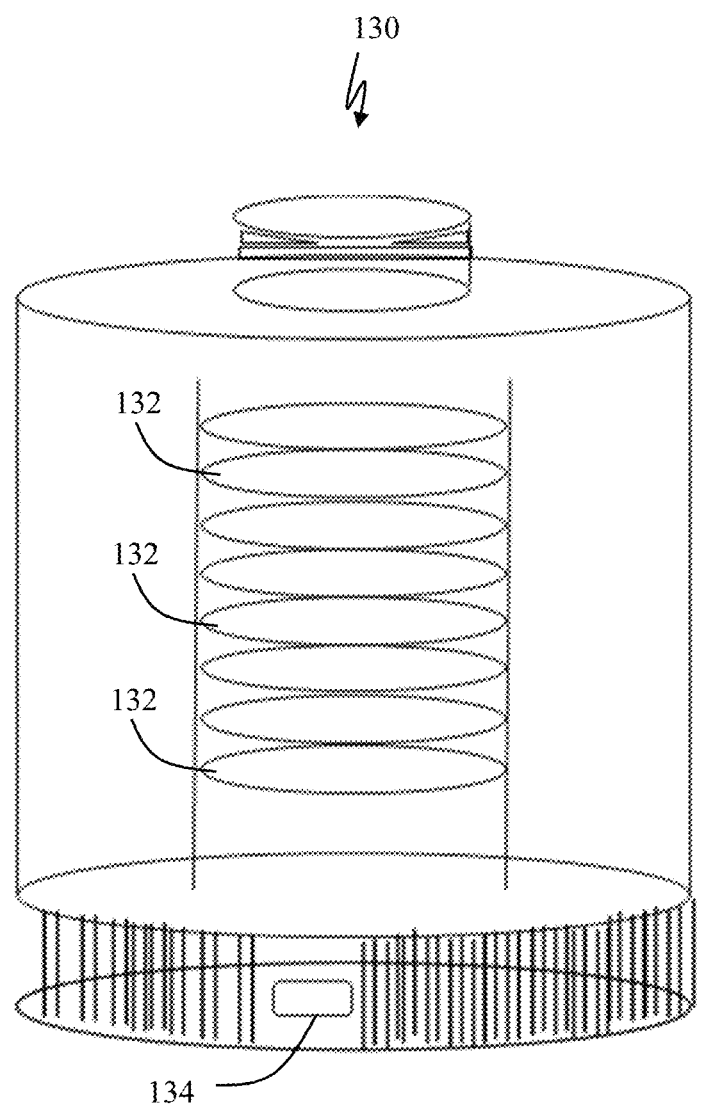
Figure 14:
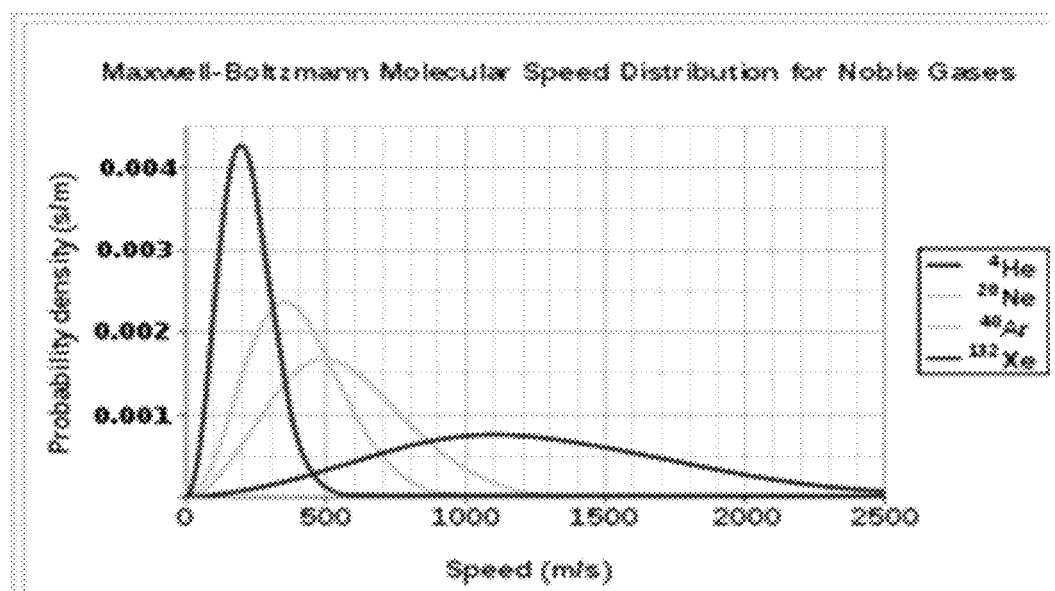
Figure 15:
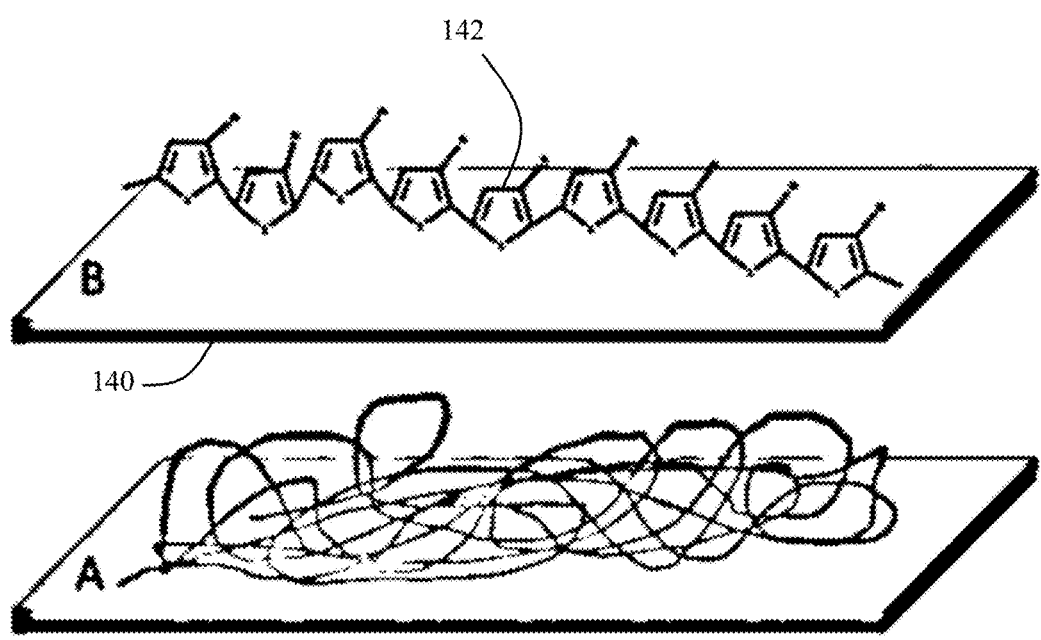

FIG. 7 is a schematic of: (top) the functionalization of the nanostructured walls of the quartz detector system (nQCM) and the response to exposure of the functionalized surface to a target analyte where the Si—OH surface bonds (step A) are reacted with a functionalized "recognition" molecule (Q) to tether it to the surface (step B) and functional group Q then interacts with the target analyte X selectively (step C); and (bottom) an example derivitization for the functionalization of a substrate without walls with aminopropyl groups, as an example of many possibilities;

FIG. 8 is a schematic of porous piezoelectronic materials according to the present invention showing, on the bottom left, a non-functionalized surface and, on the right, a chemically/biochemically functionalized surface FIG. 9 is a schematic of possible tracks for analytes through: (left) a non-functionalized porous piezoelectric material; and (right) a functionalized porous piezoelectric material;

FIG. 10 is a schematic of a layered QCM structure according to the present invention;

FIG. 11 is a schematic of a QCM device with three layers of different pore sizes with the smallest nearest the piezoelectric surface;

FIG. 12 is a schematic of a dew point detector using sensors according to the present invention;

FIG. 13 is a schematic of detector having multiple sensors according to the present invention; and FIG. 14 a graph of Maxwell-Boltzmann molecular speed distribution used in the design of sensors according to the present invention; and FIG. 15 is a schematic showing a QCM structure having: (A) a polymer on the surface of a piezoelectric material; and (B) a polythiophene polymer on the surface of a piezoelectric material according to the present invention in order to enhance selectivity of analytes.

DETAILED DESCRIPTION OF THE INVENTION

Referring to the figures, wherein like numerals refer to like parts throughout, the present invention comprises a number of approaches to improving the sensitivity and selectivity of piezoelectric sensors, including QCM sensors, as well as applications therefor. The present invention comprises various approaches that significantly increase the sensitivity and the specificity (selectivity) of piezoelectric-based sensors such as QCMs. These advances include both mechanical and chemical changes to the surfaces of the sensors. The present invention comprises the functionalization of crystals in two primary ways. First, nanoscale structures are used on the surface to improve selectivity and sensitivity for applications. Second, chemical coatings are used on the surface to improve selectivity and selectivity. The present application also includes the use of three-dimensional porous piezoelectric substrates to enhance sensitivity and selectivity. The present application also includes improvements to detectors based on piezoelectric-based sensors using phase jitter and related measurements.

By preparing an array of either identically or differentially functionalized sites on the surface, the piezoelectric detector system is able to differentiate between various molecular targets and be tuned for sensitivity to a select group of reagents at exceptionally low concentrations. For example, as the binding coefficient between a target molecule (analyte) and a functionalized piezoelectric surface increases, the detector undergoes a measurable frequency change due to the increased residence time of the target on the surface of the sensor. Very low concentrations of the analyte are expected to yield observable changes in the quartz crystal oscillation. Because the functionalization of the piezoelectric substrate is designed to respond only to one specific or a specific class of molecules, this arrangement provides a high degree of selectivity and discrimination between the desired analyte and other chemical species that might be present. The mechanical surface structures are used when phase noise is the observable of interest from collisions with inert nanostructures and the analyte. In this embodiment of the claimed invention, the sensor waveforms are in the GHz range and must be down-converted before sending them to the PLL for analysis and detection. The sensor output in this mode is a measure of concentration or pressure in the sensor environs.

The present invention also includes the use of both QCM and non-QCM-based piezoelectric materials and the application of both composite and porous materials in sensors. In summary, the present invention includes the chemical functionalization of the surface of the oscillator, nanostructural modifications of the surface to build channeled and other patterned surfaces, replacement of the quartz crystal oscillator with another elastic (or nearly elastic) piezoelectric material, replacement of the quartz crystal with a porous piezoelectric material, layering of porous materials onto quartz or other piezoelectric materials in complex assemblies, i.e., layering on a substrate (e.g., QCM). These advances allow the systems to be used for a variety of critical applications. For example, instrument configurations according to the present invention may be used for special purposes, such as dew point measurement, chemical and biomolecular detection, gaseous compound determination and DNA sampling, among others. The present invention also includes using observables such phase noise and time jitter, in addition to conventional frequency and phase changes, to greatly enhance sensitivity

EXAMPLE 1

Figure 1:
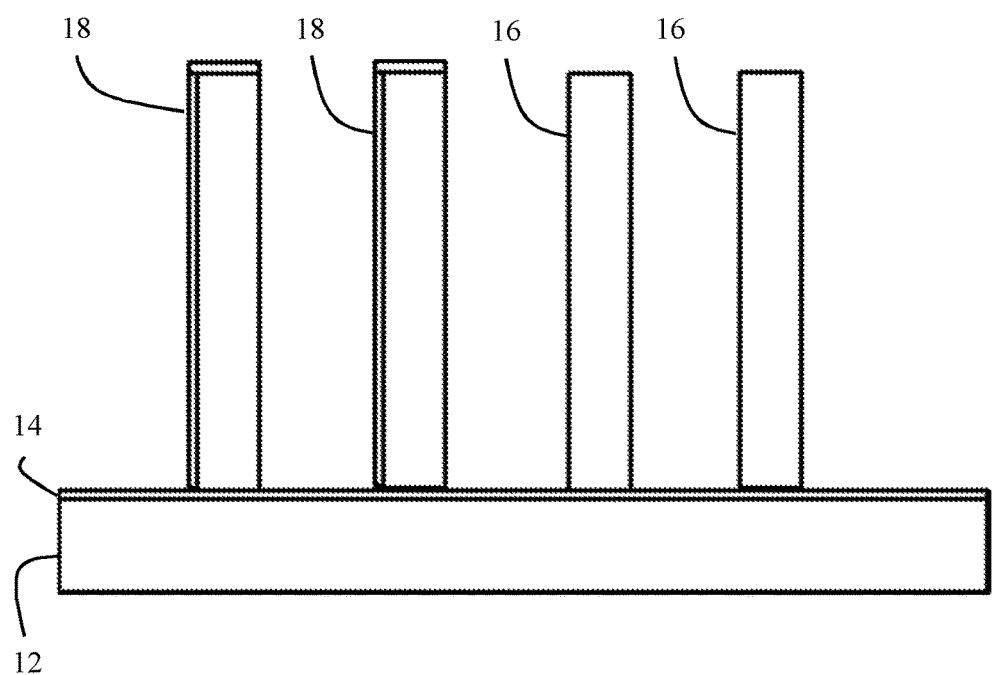
FIG. 1 is a sensor according to the present invention formed from a crystal, with or without a gold coating, and having walls of a solid material with or without a coating of a soft material on one wall and the top.

There is seen in FIG. 1 a first embodiment of the invention comprising a sensor 10 having mechanical structures thereon for improving performance. Sensor 10 comprises an AT-cut quartz crystal 12 with a thin film gold coating 14. On top of gold coating 14 are a series of nano-sized walls 16. For the sake of illustration, walls 16 are 100 nm high with width and spacing of 100 nm, and a length of 2 mm, which is a conservative estimate of the diameter of the active area of the crystal. For example, a height, spacing width and length of 1000 nm, 500 nm and 4 mm, respectively, is practical. It should recognized by those of skill in the art that different cuts may be used by crystal 12 and that coating 14 is optional and may use another substance in lieu of gold.

The material used to form walls 16 should be light in weight so as not to reduce the mass of crystal 12 significantly. $SiO_2$ is a good choice; carbon another and polymers another. In one configuration, walls 16 are hard so that molecular collisions with the surface are elastic. In another configuration, one side and the top of wall 16 is coated with a soft material 18 so that collisions with these surfaces are relatively inelastic. Either signal is easily detectable with readily available electronics. The walls may be formed using lithographic techniques or, unique to this invention, use holographic photodeposition methods to form patterned walls.

To evaluate performance, molecular dynamics may be used to determine the reaction of sensor 10 to the atmosphere engulfing the sensor 10. Assuming dry air at atmospheric pressure (760 mmHg) and a temperature of 300° K, sensor 10 is most effective at low concentrations because at high molecular density the effect of the collisions will tend to cancel because they are hitting both sides of wall 16. However, at the ppb level, there is only about a 1 in 50 chance that molecules will hit a wall at the same time, thus avoiding cancellation and improving the S/N ratio.

In order to estimate the characteristics and performance of sensor 10, a particular example is chosen with the assumptions of dry air, a pressure of 760 mmHg, and a temperature of 300° K.

Sensor Analysis

Sensor 10 may comprise an AT crystal oscillating in a shear mode at 6 mHz with an amplitude, A, of about 1 nm. A sensing oscillator is provided in a phase lock loop so that the sensing oscillator frequency is the same as the reference oscillator. However, the phase of the sensing oscillator will shift with respect to the phase of the reference oscillator. The relative phase of the oscillators is the observable metric used for sensor 10. The phase variation or phase jitter is caused by several factors:

1. Each oscillator has phase noise, so the phase difference has a noise component.
2. Temperature
3. The reference oscillator is sealed and temperature controlled to maintain a frequency stability of about 1 part in $10^7$.
4. The sensing oscillator is exposed to the environment and in particular to bombardment by the molecules.
5. Each of the molecules has momentum, which (as will be shown below) causes a phase shift of the sensing oscillator with respect to the reference oscillator.
6. If walls 16 are uncoated, then this bombardment will result in an increase in noise level. This noise, as well as the random noise of the oscillators has zero mean. The most probable rate at which the phase jitter due to the molecular collisions with the surface is a function of the mass of the molecules. The most probable rate for TNT, as an example, will be about ¼ the rate for dry air, as seen by the Maxwell-Boltzmann distribution of molecular velocities.
7. If walls 16 are coated, the molecular component of the noise will have a DC shift and require different electronics. The detector remains the same. However, in this case, the noise spectrum will not be a function of molecular speed.

The order of magnitude of each of these phase noise components, and the performance of sensor, using this design, is described below.

Sensor Parameters

Figure 2:
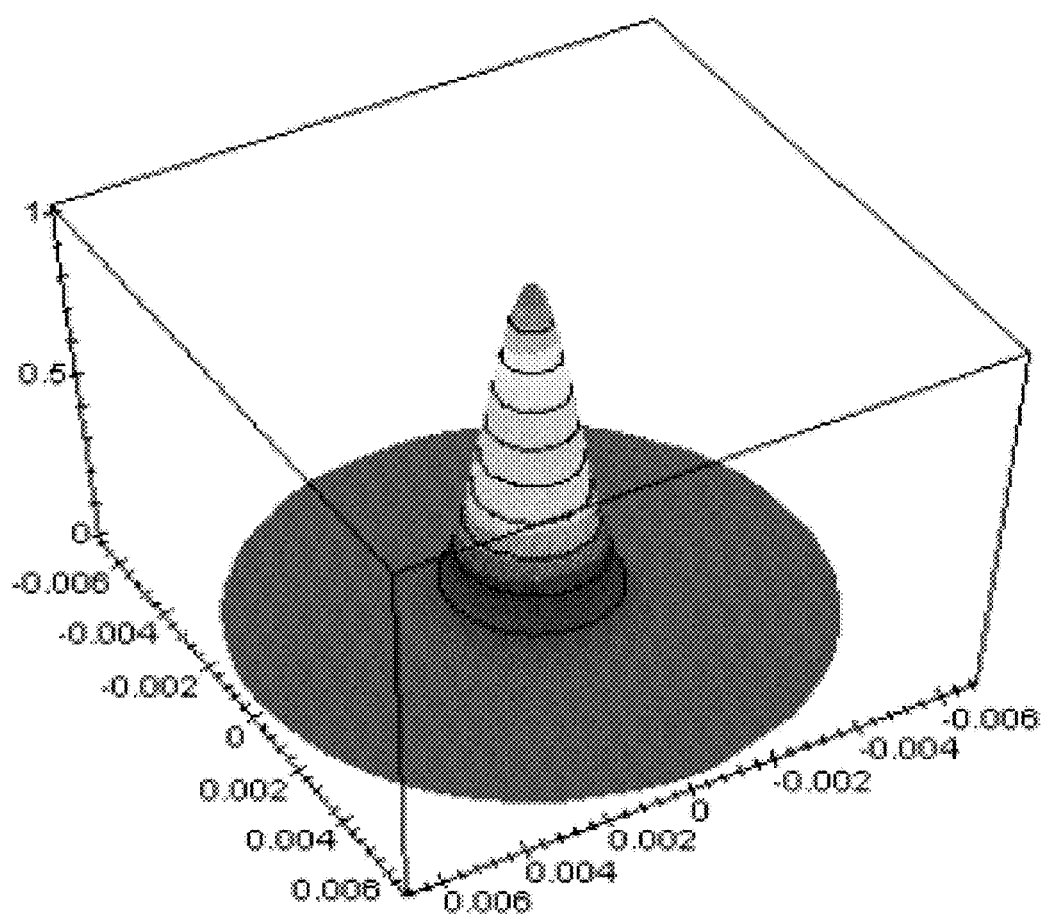
FIG. 2 is a graph of the actively vibrating area of a crystal according to the present invention.
Figure 3:
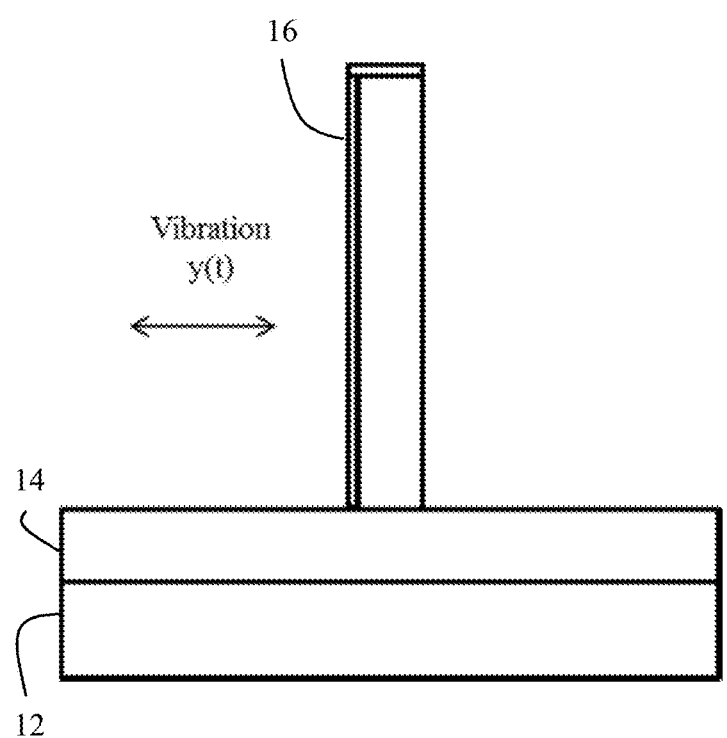
FIG. 3 is a schematic illustrating wall vibration relative to a crystal according to the present invention.
Figure 4:
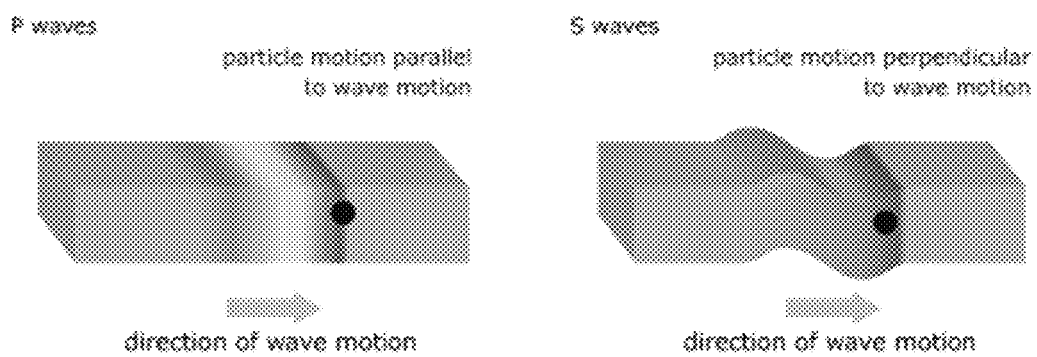
FIG. 4 is a schematic of shear mode vibration according to the present invention.

The active area of crystal 12 is shown in FIG. 2. This is where walls 16 will be positioned. Crystal 12 is vibrating in a shear mode. The mass of crystal 12 itself is about 0.005 g. Assuming that the mass of walls 16 and the vibrating portion of the crystal is about 0.0005 g, FIGS. 3 and 4 provide an illustration of the vibration characteristics of the crystal relative to walls 16 and a detailed view of the crystal motion, respectively.

Momentum

There are $2.54 \times 10^8 = 0.025 \times 10^{27} \times 10^{-17}$ molecules of dry air in the space between walls 16 of exemplary sensor 10 because the volume of the region between walls 16 is $10^{-17}$ m$^3$. The number of molecules hitting one wall 16 per nanosecond is nv/4, where n is density in #/m$^3$, and velocity is in meters/second. The area of a single wall 16 is $10^{-10}$ m$^2$. $N_{wall} = (0.25) \times (2.54 \times 10^{27}) \times 400 \times 10^{-10} = 0.254 \times 10^9$ #/sec. As an example using TNT as the analyte (although other molecules would behave and work similarly), at the ppb level, this is 0.25 TNT molecules/sec. However, it is convenient to think of this number as the rate at which TNT molecules may enter the region between walls 16; e.g., one TNT molecule every 4 sec. Because there may be on the order 20,000 walls in sensor 10, at any time there are actually $0.5 \times 10^4$ TNT molecules trapped within the spaces between walls 16. These molecules can enter at any angle and it is clear from FIG. 5 that the smaller the angle with respect to the horizontal, the larger the number of collisions for each molecule. The most probable speed of these TNT molecules is 134 nm/nsec from which the rate of collision may be determined to be in the order of 1 GHz.

Figure 5:
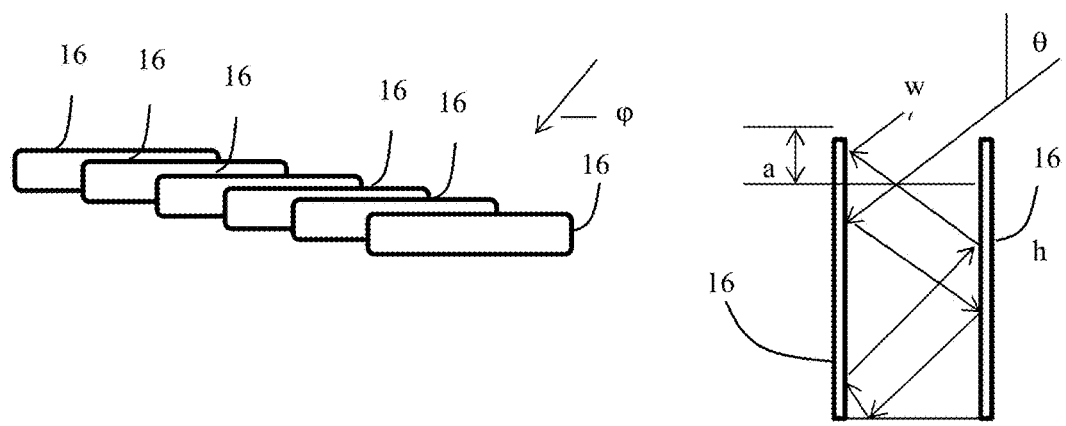
FIG. 5 is a schematic of the walls of a crystal according to the present invention and the path of a target molecule in the space between the walls.

TNT molecules are approximately 10× heavier than air molecules and 10× larger in diameter. As a simplifying assumption, they push the air molecules out of the way and follow a more or less straight line path bouncing off walls 16 as seen in FIG. 5. Although FIG. 5 depicts two dimensions, x and y, there is a third dimension, z, so each TNT molecule is ricocheting off walls 16 and along the entire length of wall 16, with the defined number of collisions. The rate of the collisions is lower as the molecules travel a further distance for θ other than 90°, which broadens the bandwidth of the TNT signal.

It is easy to estimate the number of collisions. Note that a=w tan(θ). Integer h/a is the number of hits on incoming wall 16, which is within one of the hits on opposite wall 16. Smaller θ gives more hits. A particular TNT molecule can enter the region between walls 16 at any angle and at any position between walls 16. The shallower the angle, the greater the number of collisions. Assume that the height of wall 16 is 'h' and the spacing 'w'. Assume also that each angle, position and direction is equally likely. Once the molecule enters this region between walls 16, the angle 'θ' remains constant. Note that a=w*tan(θ). The period of the wave formed by the collisions is 2a. For small angles, θ, the number of collisions of the molecules is approximately h/2a.

The chances of TNT molecules hitting a particular wall 16 at the same time is estimated as follows. Assume 5 hits per molecule, which takes ~500 nsec or $5 \times 10^5$ psec. There are $2 \times 10^4$ walls, giving $10^5$ hits in $5 \times 10^5$ psec. Assume that an elastic collision takes 0.1 psec. Then there is a 1 in 50 chance of a simultaneous collision.

The momentum of walls 16 and crystal may be estimated, assuming sinusoidal motion and amplitude of 1 nm. The equations are as follows.

$$y(t) = A(1+\varepsilon(t))\sin(\omega t + \phi(t))$$

where ε(t) is amplitude noise and φ(t) is phase noise. At a frequency of 6 MHz the peak velocity of wall 16 is Aω and the momentum, $mA\varepsilon = 1.9 \times 10^{-7}$ g-m/sec. For $N_2$ the most probable velocity is 422 m/sec and the momentum is $1.9 \times 10^{-20}$ g-m/sec. For TNT the most probable velocity is 134 m/sec and the momentum is $5 \times 10^{-2}$ g-m/sec. Thus we picture walls moving very slowly with respect to the fast moving molecules. $40 \times 10^{-3}$ m/sec for walls 16 vs. 422 m/sec for N2 and 134 m/sec for TNT. Also, for a portion of each cycle wall 16 is moving even more slowly because of the nature of the sinusoidal signal.

Momentum and Phase

Assuming elastic collisions between wall 16 and molecules, consider that each time a molecule hits a wall it is an elastic collision and there is a transfer of momentum according to the equations $$(m_1+m_2)v_1 = u_1(m_1-m_2) + 2m_2u_1$$

$$(m_1+m_2)v_2 = u_1(m_2-m_1) + 2m_1u_2$$

where $m_1$ is the mass of the molecule and $m_2$ the mass of crystal 12 and walls 16. The initial velocity is u and the final velocity v. Of course, $m_2 \gg m_1$. $v_1$ is the final velocity of the molecule and $v_2$ the final velocity of wall 16. The actual velocities of wall 16 and molecule will change very little because of their large difference in mass. However, the change in $v_2 (=\Delta v_2)$ due the TNT molecules is important. In fact, to a very good approximation, $$\Delta v_2 = 2\frac{m_1}{m_2}v_1$$

For a single TNT molecule, Δp, the change in momentum, is $8 \times 10^{-19}$ gram-m/sec. However, there are $2 \times 10^4$ walls ($4 \times 10^4$ surfaces), and a conservative assumptions is 10 hits on walls 16 before the molecule exits the space between walls 16. The result is that the Δp of walls 16 due to the collisions of TNT is $3.2 \times 10^{-13}$ gram-m/sec. This number may then be related to the jitter of the oscillator.

Phase Noise, Jitter

Phase noise or time jitter are extremely important parameters of oscillators in applications such as digital sampling, communications, radar and many others. The oscillator signal is represented as $y(t)=A(1+\varepsilon(t))\sin(\omega t+\phi(t))$, where $\varepsilon(t)$ is amplitude noise and $\phi(t)$ is phase noise.

Phase noise is also characterized as time jitter and both are extensively discussed in the literature. In the present invention, the impingement of the molecules striking wall 16 is considered as causing a change in the phase of the signal, $y(t)$. The phase noise due to the molecules will either be unidirectional or bidirectional, depending on coating 18 or lack thereof.

When molecules hit the surface of walls 16 the effect will be to change the velocity of walls 16 and the molecules. For walls 16 this change is $$\Delta v_2 = 2 \frac{m_1}{m_2} v_1.$$

Ignoring, for a moment the noise terms $m_1$ and $m_2$ the new velocity of wall 16 becomes $(A\omega+\Delta v_2)\cos(\omega t+\phi)$, and the amplitude becomes $$\left(A + \frac{\Delta v_2}{\omega}\right)\sin o(\omega t + \phi)$$

Figure 6:
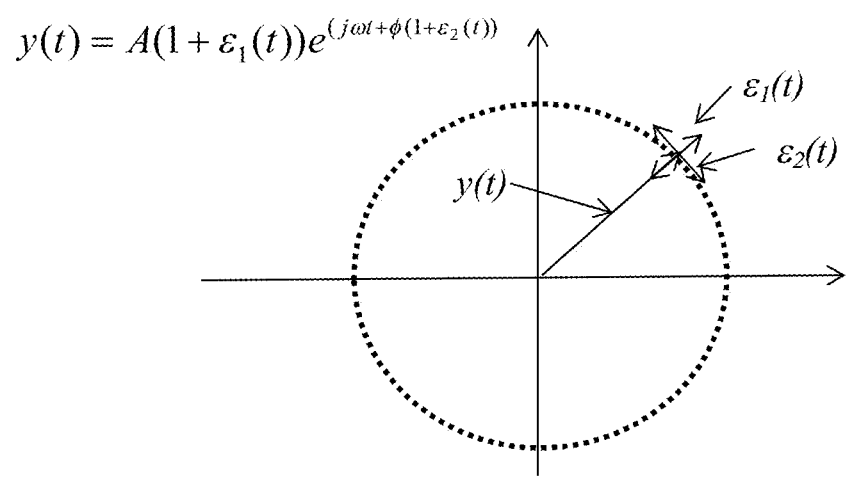
FIG. 6 is a phasor diagram of a sensing oscillator according to the present invention.

This is a change in amplitude of the oscillation. There is also a change in phase, as seen in FIG. 6.

Constituents of Dry Air

The following table shows the constituents of dry air at STP.

Molecular number density and related parameters of some materials

| Material | Number density (n) $(10^{27} \text{ m}^{-3})$ or $(10^{21} \text{ cm}^{-3})$ | (amagat) | Molar concentration (c) Units $(10^3 \text{ mol/m}^3)$ or (mol/L) | Density ($\rho$) $(10^3 \text{ kg/m}^3)$ or (g/cm$^3$) | Molar mass (M) $(10^{-3} \text{ kg/mol})$ or (g/mol) |
|---|---|---|---|---|---|
| ideal gas | 0.02504 | 0.932 | 0.04158 | $41.58 \times 10^{-6} \times M$ | M |
| dry air | 0.02504 | 0.932 | 0.04158 | $1.2041 \times 10^{-3}$ | 28.9644 |
| water | 33.3679 | 1241.93 | 55.4086 | 0.99820 | 18.01524 |
| diamond | 176.2 | 6556 | 292.5 | 3.513 | 12.01 |

Walls, 16 or other nanostructures may be built directly upon the piezoelectric surface using holographic patterns on photosensitized thin precursor coatings. It is thus possible to deposit the appropriate nanowalls on the crystal surface using holographic photodeposition techniques. This holographic photodeposition technique provides excellent control on deposition morphologies, rapid development, rapid and inexpensive fabrication and ideal wall compositions for the present invention.

EXAMPLE 2

The present invention also comprises the chemical functionalization of the surface of a sensor 10 of the present invention (e.g., QCM and other materials described below). Referring to FIG. 7, a functionalized detector 30 formed from a crystal 32 and walls 34 thereon includes chemical functionalization on walls 34, such as the attachment of tethered linkers 36 of variable lengths between walls 34 (or other appropriate substrate) and a known chemical functional group, a new chemical, and/or a biochemical molecule (e.g., riboswitches, and biological effectors, chemical functional groups, synthetic receptors) to provide for highly specific interactions with target analytes.

Detector 30 provides an excellent platform for the selective detection of key target molecules. For example, silicon dioxide ($SiO_2$) has been used as a support material to which chemical and biological sensing functionalities may be coupled. The coupling of the functionalized coatings to device surfaces can occur through several mechanisms, such as adsorption, direct covalent linkage of sensor-target molecule to detector 30, or through the use of an adapter molecule. By preparing an array of either identically or differentially functionalized sites on the surface, detector 30 according to the present invention will be able to differentiate between various molecular targets and be tuned for sensitivity to a select group of reagents at exceptionally low concentrations. As the binding between a target molecule and the functionalized surface increases, detector 30 will undergo measurable electronic piezoelectronic changes due to the increased residence time of the target on the surface of the surface. Modification of the physical and electrical properties of inorganic-organic hybrid materials is well known and thus implemented by one of skill in the art.

There are a number of reports of functionalized surfaces on QCM systems that have led to sensors with varying levels of sensitivity and selectivity for specific agents. For example, the quartz surfaces have been functionalized for the detection of volatile organic compounds VOCs, alcohols, phosphorus compounds, organic reagents and pathogens. Two general approaches are possible to detect analytes using chemically modified surfaces: (1) surface-molecule direct interactions for size/shape discrimination and (2) molecular interactions with functionalized surfaces for unique molecular discrimination. For example, airborne molecules can impact the unmodified $SiO_2$ walls of one wafer to reveal the presence of a substance with a particular molecular size and mass. Simultaneous characterization of the signature of specific molecules can be achieved when the $SiO_2$ walls are derivatized with appropriate functional groups/receptors.

The unique synthetic approach of the present invention is two-fold. As illustrated in FIG. 7, the present invention involves detector 30 having a tethered linker 36 which contains a chemical functional group on the "free" end and then reacting the functional group on tethered linker 36 to a specific sensor molecule. The functionalization of silica surfaces is well known in the literature, such as those used as stationary phases for many chromatographic techniques. Organofunctional silica and quartz surfaces has been prepared through the reaction of an appropriate organofunctional silane directly with the silicate that then reacts to add a new "head group" to the tether that then reacts with the desired analyte, as shown schematically in FIG. 7. These inorganic-organic hybrid materials can be used to build the functionalized surface of the quartz system. The functionalized surfaces of silica nanoparticles has been shown useful for several applications including stimuli-responsive applications. Other surfaces beside silica can also easily be functionalized. For example, replacing the siloxane "head" group (the end to be attached to the surface) on the tether with a thiol group will link strongly to gold surfaces. Similar synthetic strategies are possible with many other solid state surfaces. As shown in FIG. 7, the Si—OH surface bonds (step A) are reacted with a functionalized molecule (Q) to tether it to the surface (step B). Functional group Q then interacts with the target analyte X (step C).

Surfaces can be designed to interact uniquely with agents of interest, including both chemical and biological materials. Newly proposed for the present invention are specific chemical and biological receptors, tethered to the surfaces to provide high levels of selectivity. For example, one application is to incorporate artificial riboswitches into the functionalized surfaces of the QCM system (denoted ƒQCM). Artificial riboswitches have recently been shown to be effective in the regulation of DNA and RNA viruses but, using our unique approach, ƒQCM systems should be preparable that could be used to both detect and continuously monitor the operation of pathogenic DNA or RNA-based viruses. Additionally, specific riboswitches or aptamers could function as highly sensitive and selective detectors for biological threat agents in remote (automated) monitoring environments. In forensic settings, these components could be used for rapid species identification (e.g., plant and animal matter) as well as for geospatial tracking applications. In a similar fashion, biological effector molecules (small molecules that bind selectively with a regulatory chemical) may be incorporated into ƒQCM units that would provide high selectivity and sensitive for biological components, e.g., small organic molecules, proteins, cells, fungi, bacteria, etc. By using these highly selective and relatively small biological "sensors" (riboswitches or molecular effectors), it should be possible, through linkages to ƒQCM systems, to produce rapid, highly selective, and very sensitive detector systems for RNS and DNA fragments, bacterial, viruses, fungi, plants and other biological signatures.

A second approach is to use other functional groups to add to the silica so that the surface is functionalized with alkane, alkene, amine, cyano, ether, thio, ester, alcohol, phospholipid, amino acid and sulfite functional groups, among others. These would be highly selective for agents such as organophosphorous compound, VOCs, toxins and others, depending on the specific group chosen. As another example, a dicyanovinyl-functional group was synthesized that will react selectively with cyanide to form a highly effective cyanide detector.

Antibodies have also been linked to QCM surfaces in a straightforward process and have been used, for example, to detect several bacteria, including *Vibrio harveyi* and *Campylobacter jejuni* strains. Using this approach, other pathogenic species can be selected for, especially agents involved in biological warfare. When used in a multi-QCM array where each QCM unit or even part of a QCM unit is functionalized to react with just one particular strain, it should be possible to build rapid response broad ranging sensor for a large range of species.

An additional possibility of this arrangement is that chiral functional groups can likewise be attached to the modified silica surface of the detector. This approach has been highly successful in the chromatographic detection and isolation of chiral molecule using HPLC and related techniques. In addition, an L-phenylalanine-coated QCM molecular assembly was used to provide high selective recognition of L-mandelic acid. In essence, the functionalized silica walls of the quartz detector system acts as a chiral stationary phase that can discriminate between enantiomer and diastereomeric components. Since most biological and many organic molecules of interest are chiral, this specific capability could lead to important rapid information about the chirality of the analyte.

EXAMPLE 3

In another embodiment of the present invention, the quartz crystal oscillator is replaced with another elastic (or nearly elastic) piezoelectric material, such as piezoelectric composite polymers [or piezocomposites] (e.g., PZT/polymer composites, PMN-PT based composites, and ZnO nanocomposites), piezoelectric amorphous polymeric films on rigid backers (e.g., polyimide and polyvinylidene chloride (PVDC)), semi-crystalline polymers (e.g. polyvinylidene fluoride (PVDF), polyamides, liquid crystal polymers and Parylene-C), ceramic and metallic piezoelectric materials, and similar materials.

A variety of piezoelectric materials are known that provide different properties relative to the typical QCM substrate for sensing applications. Two ways to increase the sensitivity of the detector are to: (1) increase the ratio of the analyte mass relative to the mass of the oscillator, and (2) increase the number of specific interactions between the surface and the analyte.

The well-known Sauerbrey Equation ($\Delta f = -C_f \Delta m$ where $C_f$ is the sensitivity factor of the crystal) describes that a change in crystal frequency as proportional to the change in mass of the crystal. Therefore, increasing the ratio of the analyte mass relative to the mass of the oscillator should allow for a higher response. In effect, the intensity of the inertial field developed on the crystal surface during crystal vibration is directly affected by the presence of the analyte.

Increasing the number of reactive sites (RS) on an area of the sensor, which is available for reaction with an analyte, increases the probability of an interaction and a successful "detection event". The Sauerbrey equation, however, still holds since the sensitivity of the detector is defined as the frequency change as a function of change in mass per unit area, M', of the sensor (Note that the total mass, M, attaching to the RSs and $dF = -K\, dM'$. The effect on sensor response is similar to a rate equation describing a chemical reaction where increasing the concentration of the detector receptor sites increases the response of the detector to an analyte. The corresponding sensor effect may be best explained using phase changes rather than frequency changes as the primary observable. When a molecule hits a RS, it can either react or rebound. If it rebounds there is a phase disturbance of the oscillator waveform, manifested as phase noise. If, however, it reacts, then the phase disturbance is "remembered" by the oscillator, and results in a frequency change in addition to an increase in phase noise. Thus, there is an increase in dF/dt, an effect similar to a change in rate of a chemical reaction.

Piezoelectric polymers are well known and can be prepared as relatively thin materials. Amorphous and semi-crystalline polymers can provide a lightweight surface for sensing. Additionally, these polymeric materials can be further functionalized to enhance selectivity for specific analytes (see above). Functionalizing these surfaces would provide a lightweight material that should increase sensitivity. Additionally, preparing composite inorganic/organic hybrid materials further extends the range of possible interactions. Ceramic piezoelectric materials are available and are well known in transducer applications.

EXAMPLE 4

In yet another embodiment, the present invention includes a porous piezoelectric sensor 50 in lieu of a quartz crystal. Sensor 50 may be formed from porous piezoelectric ceramics (e.g., lead zirconate titanate (PZT) and nanoporous silica), porous piezoelectric polymeric materials (including composites), semi-crystalline polymers (e.g. polyvinylidene fluoride (PVDF), polyamides, liquid crystal polymers and Parylene-C), porous piezoelectric void-charged composite polymers (e.g., Cellular polypropylene, porous PTFE, and multilayer PDMS VCP), and Xerogel, sol-gel, nanoscale piezoelectric materials, and similar.

Porous piezoelectric sensor 50 forms receptor sites 52 that use the interior surfaces of the oscillator to increase the effective surface area of the sensing surface. Increasing the concentration of the receptor sites 52 increases the response (rate) of the detection system to an analyte. In a first-order approximation, the number of receptor sites on sensor 50 is proportional to the detector response through a chemical rate law-type expression: Response=k[analyte] [detector receptor sites] (n. b., square brackets indicate concentrations, for sensor 50 it is refers to the surface area sites available for analyte-receptor reaction). Thus, increasing the surface area per mass of the oscillator, such as by using a porous material, would increase the detector response rate (sensitivity). For example, porous silica is known to have surface areas as large as 800-1000 $m^2/g$ relative to the sensing surface of a QCM detector of approximately $1.4 \times 10^{-3}$ $m^2/g$. The difference is, therefore, over $10^6$ in increased surface area/mass in the porous materials relative to a basic QCM approach. The actual realized advantage, however, may be even greater since the porous material could be used in a thicker arrangement than a typical QCM to provide more surface sites per sensor unit. Simply increasing the thickness of sensor 50 to 2 mm would potentially gain an additional 10-fold increase in available surface sites. Referring to FIG. 8, these interior surfaces may be simply native non-functionalized pores 54 or functionalized pores 56 using the methods described above for functionalization. In addition, mesoporous materials with silica "tubes" functionalized in the interior may be employed for sensor 50.

Piezoelectric porous sensors 50 may have sizes ranging from several nanometers to multi-micron or larger sizes. The pore size can be controlled either during the preparation process or post-synthesis processing. Two possibilities for the operation of such devices exist. In the first arrangement, the analyte is passed through the substrate, similar to a filtration process. The analyte then interacts with the oscillating porous material to generate a signal (n.b., porous is used here as a generic term to include nanoporous, mesoporous, and macroporous systems). The great advantage results from the enormous increase in available surface sites relative to a quartz surface. In the second arrangement, the analyte does not pass completely through the porous material but does enter the material and interacts either through a size exclusion process or by a chemical interaction/reactive process. The advantage of this embodiment of the invention is that it is possible to select for both the size and the reactivity of an analyte, while taking advantage of an increased surface area.

In the case of the non-functionalized material, illustrated schematically in FIG. 9A, the smaller analyte (particle A) passes through sensor 50, colliding with the internal walls of receptor sites 52 of sensor 50. The smaller the analyte, the fewer receptor site 52 internal wall collisions. Larger analytes will have more wall collisions until the analyte size exceeds the size of receptor site 52 and is thus excluded from the pore, as seen with particle B of FIG. 9A. In a functionalized pore 54, similar sized molecules will have differential interactions depending upon their chemical composition. Analytes with only weak interactions will pass readily through the material, as seen in with particle A in FIG. 9B. An analyte with a greater chemical affinity to the functional groups in the functionalized oscillator, particle B of FIG. 9B, will have far more interactions. Finally, an irreversible reaction between the analyte and the functionalized substrate would trap the analyte in the media, such as seen with particle C in FIG. 9B.

EXAMPLE 5

In yet another embodiment, the present invention comprises the three-dimensional building or layering of porous materials onto quartz or other piezoelectric materials in complex assemblies. The layers on the substrate (e.g., QCM) may include porous piezoelectric ceramics (e.g., lead zirconate titanate (PZT) and nanoporous silica), porous piezoelectric polymeric materials (including composites), semi-crystalline polymers (e.g. polyvinylidene fluoride (PVDF), polyamides, liquid crystal polymers and Parylene-C), porous piezoelectric void-charged composite polymers (e.g., Cellular polypropylene, porous PTFE, and multilayer PDMS VCP), and Xerogel, sol-gel and nanoscale piezoelectric materials In this embodiment, porous materials may be layered directly onto a piezoelectric substrate. This provides more sites for functionalities as well as some level of size differentiation. For example, mesoporous silica with a monodispersed hexagonal lamelliform was coated onto a QCM surface to form a relatively thin layer that was a highly sensitive moisture sensor. Similarly, a layer of a porous $Al_2O_3$ film used with a polymeric poly(ethylene imine) (PEI) was deposited onto a QCM surface using a low temperature sol-gel process. This sensor was used to detect $CH_3SH$ at the 100 ppb level.

The layering process onto a QCM device can include: (1) other porous media and polymeric films, (2) the layering of magnetoelectric films for magnetic measurements and differentiation, (3) heteromorphic designs with multiple layers of similar or different materials layered on the substrate (4) building up three-dimensional tethered structures to the surface with multiple recognition (receptor) site. The types of materials include those described previously including: (1) porous piezoelectric ceramics, (2) porous piezoelectric polymeric materials (including composites), (3) semi-crystalline polymers, (4) porous piezoelectric void-charged composite polymers, (5) porous non-piezoelectric materials (e.g., ceramics, polymers, and (6) xerogel, sol-gel and nanoscale piezoelectric materials. Additionally, functionalized dendrimers and hyperbranched polymers will provide three-dimensional tethered structures to the surface with multiple receptors per surface attachment point.

The multi-layer designs provide a great deal of design flexibility. For example, as shown in FIG. 10, differentially functionalized media can be layered onto the QCM surface 70 with each layer 72, 74 having different chemical specificity. In another approach, layers of materials of differing pore sizes 76, 78, 80 can be layered on the surface providing conceptual "V-shaped" channels on the surface, as shown in FIG. 11. Molecules of different sizes and chemical functionality can penetrate into the porous material to different extents. Adding surface functionalization that can be different for each layer can provide even greater specificity. This arrangement may also enhance the shear oscillation of the system. Additionally, the system could also be set to oscillate in different planes and differently for the various layers (FIG. 10). The use of different solid state and materials strategies according to the present invention can provide unique sensitivity and selectivity for piezoelectric-based detectors and sensors.

EXAMPLE 6

Referring to FIG. 12, the present invention includes an improved dew point detector 90. A pair of stands 92 and a metal plate 94 extending there between form a chassis 96 for detector 90. First and second airtight enclosures 98 and 100 are attached to plate 94. First enclosure 98 contains a reference crystal 102. Second enclosure 100 contains a sensor crystal 104 and a dual element Peltier cooler 106. A pipe 108 coupled to second chamber 100 allows external air to enter second chamber 100 and contact the top of sensor crystal 104. A heat sink 110 and fan 112 are positioned under second chamber 100 to remove heat from dual element Peltier cooler 106. Warm air flowing across heat sink 110 warms chassis 96, the inside of first chamber 98, and thus reference crystal 102, to keep reference crystal 102 slightly above room temperature. A hole 114 in chassis in communication with second chamber 100 and along the flow of warm air from heat sink 110 acts as a venturi to provide a vacuum that draws outside air into pipe 108.

Temperature Control of Right Hand Chamber

A temperature sensor 116 is connected to the upper element of dual element Peltier cooler 106, which, by design, is configured to be lower in temperature than the lower element of dual element Peltier cooler 106. Dual element Peltier cooler 106 is used to ensure that the temperature of sensor crystal 104 is lower than the rest of second chamber 100 so that when dew forms on sensor crystal 104 it will not form in the rest of second chamber 100.

A unique feature of this design is the manner in which dew point is detected. When dew begins to form on sensor crystal 104, the initial onset of water molecules onto sensor crystal 104 produces a large phase noise in the crystal oscillator signal. This occurs before a change in the frequency is detected. This phase noise signal is fed to the temperature controller so that the operation remains in the noisy state where only parts of sensor crystal 104 are coated with the water molecules and thus provides a molecular level measure of dew point.

Condensation Spectrometer

Detector 90 can also be configured to detect the condensation point of other materials and thus serve as an indicator of unknown gases in the atmosphere surrounding the sensor. A kind of reverse distillation process. In the case of two gases, e.g., the gas with the higher condensation temperature would first coat the sensor, and then the second gas with the lower condensation temperature would form on the surface, now coated with the first material. The same noise signal would occur for the second condensation as the first.

EXAMPLE 7

In a further embodiment, the present invention may be used to detect multiple target analytes simultaneously. As seen in FIG. 13, a contaminant detector 130 may configured to be include multiple functionalized sensors 132, each functionalized differently. A heat source 134 may be positioned below sensors 132 and is used to heat samples so that a chimney effect carries analyte vapor up through sensors 132, each with a specific coating for functionalization, whether chemical or nanostructure, as described herein. Alternatively, analyte flow could be created by a fan or similar means. Collected data may be sent via Bluetooth, for example, to a tablet or other smart device for cloud processing, such as by neural network processing, with results displayed on the smart device. Structure 134 would be particularly appropriate for testing suspected drugs samples in the field and vastly superior to present methods. Fan would be used in lieu of or in addition to oven to enhance general monitoring of an environment. Contaminant detector 130 could be packed into a small size, including the requisite detector circuitry and power source, for operating sensors 132, oven 134 and any fan. Molecular adsorption in the sensor in FIG. 13 can occur on the sensor either differentially or exclusively. In the differential use, an array of sensor crystals is employed, where each crystal has a different surface coating that variably adsorbs the volatile gases. While all chemicals in the sample may be absorbed by any particular coating, each different coating interacts to varying degrees with the component analytes. This leads to different amounts of surface adsorbed gas components on each of the sensor crystals that can be computationally separated. In contrast, using an exclusive adsorption approach, an array of PZ-sensor crystals is again employed but, in this case, each sensor reacts uniquely and exclusively with just one component of the mixture. This allows for the straightforward determination of the concentration for each component by simply monitoring the signal change from each specific sensor crystal.

Crystals are functionalized chemically, mechanically (nanowalls) or both and thus can provide a wide spectrum of signals to send to the neural network for analysis. Clearly, there are a wide variety of chemical coatings that could be used to provide a spectrum of responses. There are also a wide variety of nanowall structures that could be considered, also providing a spectrum of responses. In this case, the underlying physical property of molecules providing the discriminant is the Maxwell-Boltzmann distribution of molecular velocity as a function of mass, shown in FIG. 14. The mass of the molecule determines the most likely speed (peak of the distribution). The idea is that as the molecules are ricocheting between the walls, the wall spacing and the molecular speed will determine a signal frequency associated with a particular molecule. Typically such frequencies are in the GHz range, but present day electronics would easily provide the instrumentation needed to detect such signals. There could be different wall spacing on each crystal, or a single crystal could have several spacings. The spectrum would be computed using an FFT (Fast Fourier Transform) and the interpretation of the spectrum be the task of the neural network.

There are several considerations in such a scheme the most important being that the M-B distribution is rather broad so that useable specificity would rely heavily on the signal processors and the neural network. Also, the density of the contaminant must be low enough, so that the likelihood of a molecule of interest hitting both sides of a wall simultaneously is low to avoid signal cancellation. Air molecules, e.g., are so plentiful that signal cancellation is virtually guaranteed. However, molecules present in the ppb range would have a small likelihood of hitting both sides of a wall simultaneously and thus produce a discernable signal.

Another way in which the nanowalls could be configured is to coat the top and one side of each wall which a "soft" material which would reduce the effect of the impact on these surfaces, and thus avoid signal cancellation. This would be a suitable structure for the case in which the contaminant density is high. But, in such a structure, specificity is lost because there would be no ricochets in the space between the walls.

These are some of the instrument concepts which would be practical with the new sensors, using phase, rather than frequency as the primary observable. However, in all of these configurations there will surely be "crosstalk" among the sensors, in the sense that each sensor will respond to a set of molecules. But, there will be a different set for each of the sensors which the neural network will sort out.

The neural network is important to the success of this approach. However, equally important is the fact that that the sensor provides a meaningful representation of the physical signals (molecules striking something) and also that the sensor provides an observable which is an unambiguous rendering of the events. Without these guarantees there would be no chance for the neural network to sort out the overlapping responses.

Remembering that the sensing oscillator is embedded in a PLL, the output of the comparator before collision is the product $A\sin(\omega t+\phi) * B\sin(\omega t)$, which for B=1, and keeping only the low frequency terms is $$\frac{A}{2}\cos(\phi).$$

This is the value of the control signal which keeps the PLL in lock. Perturbations in the frequency of the sensing oscillator would normally cause $\phi$ to change to maintain lock.

In a sensor according to the present invention, the action of the molecule is to cause the amplitude of the control signal to change by an amount $$\frac{\Delta v_2}{\omega}.$$

If we design the PLL so that under normal conditions $\phi=45°$ (this choice is arbitrary) then we can relate the amplitude change due to the molecules to an equivalent phase change or time jitter.

In our case this ratio is $4.4\times10^{-7}$. The cycle time of the oscillator is $0.166\times10\times10^{-6}$ sec. Therefore the time jitter is in the order of 0.7 psec. The phase jitter is $28\times10^{-7}$ radians. These are the same order of magnitude larger than commercially available AT cut crystal oscillators.

EXAMPLE 8

The nQCM system according to the present invention provides an excellent and unique platform for the selective detection of key target molecules. Silicon dioxide ($SiO_2$) has been used as a support material to which chemical and biological sensing functionalities may be effectively coupled. The coupling of the functionalized coatings to nanostructured QCM devices can occur through several mechanisms, such as adsorption, direct covalent linkage of sensor-target molecule to the $SiO_2$ surface, or through the use of an adapter molecule.

Previous work with QCM sensors has shown that they are very sensitive to atmospheric water content at the sensor surface. While water concentrations in the atmosphere vary with weather patterns, sensing an unusually high water vapor concentration in the presence of one or several monitors when compared to a spatially removed reference would provide one useful marker. Atmospheric $CO_2$ concentrations are more stable over time and the detection of significantly increased $CO_2$ signals would be another important component of the signature. $CO_2$ sensors have long been explored and a polymeric or heteropolysiloxane functionalized QCM system could readily be prepared and employed to selectively detect $CO_2$ exposure in our proposed QCM system.

The detection of endogenous human gases beside the emitted water and $CO_2$ is critical to the proposed system. From previous studies, ammonia was found to be the major metabolite in exuded human breath at level about 800 ppb, followed by acetone (500 ppb), methanol (450 ppb), ethanol (100 ppb), isoprene (100 ppb), propanol (20 ppb), and acetaldehyde (20 ppb). Each of these higher concentration relatively abundant hydrocarbons chemicals are well within the QCM operating range and can be used to form a unique human breath exposure signature. Thus, in our functionalization scheme, ammonia may be detected through the use of a QCM surface functionalized with pyrrole, aniline or $SnO_2$ tethered components (vide infra). In support of this concept, a substrate coated with an ammonia sensitive polymer has been previously reported to be successful in ammonia detection. Using our chemically functionalized QCM-surface strategies, we should be able to develop unique signatures for human breath exposure employing the detection of these species.

It has been long known that endogenous human chemical signatures can be reliable predictors of early-stage medical conditions including, cancer, diabetes, heart disease, infection and many others. Measuring components from human breath, sweat, and body fluids, can detect disease states long before they are found via current imaging and biochemical modalities, providing an effective diagnostic metric. The approaches of the present invention provide a unique platform for the rapid, accurate and inexpensive detection of key biochemical markers (ppb) with high selectivity/identification. The present invention can provide a range of biochemical markers accessible at the ppb level in <10 sec. analytic time. Use of porous systems as described herein could increase response sensitivity by up to 106. The invention is also networkable with remote operation possible The advances described above allow for sensors that may be used in new systems for a variety of critical applications. For example, instrument configurations according to the present invention are useful for special purposes such as dew point detection and DNA sampling. The present invention provides for rapid, inexpensive and simple analysis of key biochemical/chemical markers arising from early stage medical conditions. The present invention may be used for a range of biochemical markers accessible at the ppb level in <10 sec. analytic time. The present invention may thus used for biologically specific nucleotide interactions by tethering complimentary DNA nucleotides to surface. When complimentary base interacts with the tethered nucleotide, the signal is generated. In addition, the use of porous systems describe above could increase response sensitivity by up to $10^6$.

Similarly, the present invention may be used for rapid, robust, inexpensive and networkable multi-agent sensor/detector system that can be used in either a passive or active (constant) mode. The present invention has high sensitivity (e.g., ~1 ppt @STP), is robust, multi-agent capable and is low-cost technology based on solid-state sensor system. Small sensor and SOC circuitry can result in a package size ca.<2 in. Surface (or porous interior) can be functionalized to detect specific chemical/biochemical species through various surface-analyte interactions. In addition, the present invention can employ mechanical (nanostructured surface) and/or chemical surface functionalization (provides specificity) with multi-agent capability in one system. The present invention thus provides the potential for exceptional sensitivity (1 ng/cm$^2$) response time, robustness and agent selectivity at low cost that operates on gas or liquid phases in extreme environmental conditions.

EXAMPLE 9

The present invention may be used for rapid DNA nucleotide or biomolecule analysis. Forensic and medical application now require the rapid determination of single nucleotides for analysis of variations among individual genomes with medical and/or personal identification uses. Single nucleotide polymorphisms (SNP) are highly conserved, widely distributed and common (1.42 million SNPs have been identified), providing unique human signatures, far better than STR sites. The present invention can provide a new generation of genetic indicators for clinical diagnosis and prognosis and for unambiguous forensic identification. The present invention provides for a specific, rapid, sensitive, inexpensive approach and does not suffer from previous limitations. More specifically, the approach of the present invention involves biologically specific nucleotide interactions by tethering complimentary DNA nucleotides to surface. When a complimentary base interacts with the tethered nucleotide, a signal is generated indicating detection of the complementary base. Sensitivity should be in the ppb level in flow system. Selectivity is based upon very specific biological base-pair interactions and recognition, and would not require spectroscopic, spectrometric, radioactive, conformation or chromatographic methods.

EXAMPLE 10

The present may also include piezoelectric materials having surface coatings adapted for $CO_2$ gas sensing applications, such exhaled gas detection. In this approach, polymeric or other thin film materials are applied to the surface of a sensor 140 as a coating 142. Each coating 142 has a different, although non-exclusive, interaction with the various components of the $CO_2$ and exhaled gas (EG) mixture. Coating a number of crystals, each with a different adsorbing material, and arranging them as seen in the detector 130 of FIG. 13 yields a differential uptake for each component on the crystal surface that can then be readily deconvoluted using data from the array of sensors 140.

The selective adsorption of gases by polymers is a well-known process with a well-established literature, primarily studied for gas stream purification, industrial stream monitoring and separation chemistry. Polymers, such as polysiloxanes, polythiopehenes, polyanilines, nanotubes, and related species, bound to piezoelectric surfaces will provide high selectivity for $CO_2$ molecules, as illustrated in FIG. 15. For example, $CO_2$ is known to selectively bind with surface polysiloxanes, polyamine, and polythiophenes while surface-bound nanotubes are highly efficient and selective for hydrocarbon (EG) adsorption. These polymers readily bind to quartz surfaces, are easily synthesized and are expected to be excellent media for differential gas sensing. A number of similar polymers have been reported successfully binding to QCM devices, such as polysiloxanes for toxic organophosphate vapor analysis, polythiophenes for aromatic hydrocarbon detection, and polyallylamine hydrochloride for ammonia detection. As an example, divinyl units have been successfully tethered to QCM surfaces for specific HCN detection.

The differential adsorption of gases on a given crystal may also be easily modulated by using a combination of different polymers co-mixed onto a single sensor head. By tailoring the polymer mixture on each sensor crystal and knowing the gas adsorptive properties of each polymer component, it is possible to modify the differential adsorption of each analyte gas on the crystal's surface. By using a small sensor array, such as that seen in FIG. 13, and with each crystal displaying different gas adsorption properties, it is possible to readily simplify and facilitate a gas concentration analysis without adding cost or complexity.

Multi-layer designs also would provide a great deal of flexibility, if needed as a backup to the other strategies described. For example, as shown in FIGS. 10 and 11, differentially functionalized media can also be layered onto the QCM surface with each layer having different chemical/size specificity. Molecules of different sizes and chemical functionality can then penetrate into the porous material to varying extents with different retention and adsorption characteristics—perfectly suited to our analytic approach.

What is claimed is:
1. A detector, comprising:
   a chassis;
   a first chamber mounted to the chassis and enclosing a reference sensor comprising a first quartz crystal having a first upper surface and a first plurality of upstanding walls positioned on the first upper surface, wherein the first plurality of walls have a first height of up to 1000 nanometers, a first width of up to 1000 nanometers, and are spaced apart from each other by up to 1000 nanometers;
   a second chamber mounted to the chassis and enclosing a cooling element, a temperature sensor mounted to the cooling element, and a detection sensor positioned on the cooling element and comprising a second quartz crystal having a second upper surface and a second plurality of upstanding walls positioned on the second upper surface, wherein the second plurality of walls have a second height of up to 1000 nanometers, a second width of up to 1000 nanometers, and are spaced apart from each other by up to 1000 nanometers;
   wherein the second chamber includes an inlet for the flow of air into a top of the second chamber and an outlet for the flow of air out of a bottom of the second chamber so that when the detection sensor is cooled by the cooling element and air is drawn into the inlet and out of the outlet, molecules in the air will be deposited on the detection sensor.
2. The detector of claim 1, further comprising a second cooling element associated with the second chamber and configured to maintain the second chamber at a temperature different than the first cooling element maintains the detection sensor.

3. The detector of claim 2, further comprising a heat sink positioned below and proximately to the second chamber.

4. The detector of claim 3, further comprising a fan positioned to blow across the heat sink and the outlet to create a vacuum proximately to the outlet.

5. The detector of claim 4, a temperature sensor associated with the second cooling element.

* * * * *